United States Patent
Hägel

[11] Patent Number: 4,864,064
[45] Date of Patent: Sep. 5, 1989

[54] PROCESS FOR THE PREPARATION OF TERT. ALKYL-TERT. ARALKYL PEROXIDES

[75] Inventor: Eberhard Hägel, Icking, Fed. Rep. of Germany

[73] Assignee: Peroxid-Chemie GmbH, Hoellriegelskreuth, Fed. Rep. of Germany

[21] Appl. No.: 100,200

[22] Filed: Sep. 23, 1987

[30] Foreign Application Priority Data

Sep. 30, 1986 [DE] Fed. Rep. of Germany ....... 3633308

[51] Int. Cl.$^4$ .......................................... C07C 179/06
[52] U.S. Cl. ..................................................... 568/558
[58] Field of Search ........................................ 568/558

[56] References Cited

U.S. PATENT DOCUMENTS 3,267,066 8/1966 Tijssen ................................ 568/558

FOREIGN PATENT DOCUMENTS 2016108 10/1971 Fed. Rep. of Germany.
954361 4/1964 United Kingdom.

OTHER PUBLICATIONS

Noller et al., *Analytical Chemistry*, vol. 35, No. 7, pp. 887–893, (Jun. 1963).
*Encyclopedia of Chemical Technology*, (Kirk–Othmer), 3rd ed., vol. 23, pp. 492–493, (1983).

*Primary Examiner*—Bruce Gray
*Attorney, Agent, or Firm*—Felfe & Lynch

[57] ABSTRACT

Disclosed is a process for the preparation of tert. alkyl-tert. aralkyl peroxides with the general formula

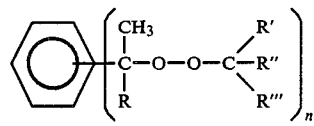

where R represents an alkyl radical with 1 to 4 C-atoms, R', R" and R'" represent the same or different alkyl radicals with 1 to 5 C-atoms and n is a number from 1 to 3, by reacting an olefin with the general formula

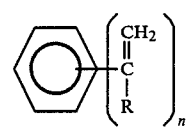

with a tert. alkyl hydroperoxide with the general formula

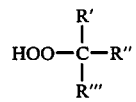

where R, R' and R" and R'" and n having the meaning indicated above the presence of aqueous hydrochloric acid.

11 Claims, No Drawings

PROCESS FOR THE PREPARATION OF TERT. ALKYL-TERT. ARALKYL PEROXIDES

BACKGROUND OF INVENTION

The present invention is in a process for the preparation of tert. alkyl-tert. aralkyl peroxides with the general formula I

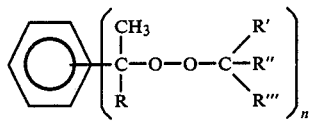

where R represents an alkyl radical with 1 to 4 C-atoms, R', R" and R"' represent the same or different alkyl radicals with 1 to 5 C-atoms and n is a number between 1 and 3. In the process of the invention an olefin with the general formula II

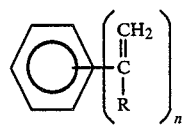

is reacted with a tert. alkyl hydroperoxide with the general formula III

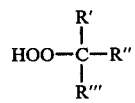

where R, R', R" and R"' and n have the meaning indicated above.

Tert. alkyl-tert. aralkyl peroxides are capable of forming relatively stable radicals at relatively high temperatures and are, therefore, particularly suitable as initiators for cross-linking synthetic resins. Moreover, they have the advantage of not forming decomposition products with unesireable properties. Processes for their preparation have, therefore, been known for some time. In particular, processes are widely used in the case of which a tert. alkyl hydroperoxide is condensed with the corresponding carbinol. A disadvantage of this process is that the carbinols have to be first produced from the corresponding hydroperoxide by reduction and that the diols and triols are solid compounds which are difficult to use in controlled amounts.

It is also known, e.g. from DE-OS 20 16 108 to prepare tert. alkyl-tert. aralkyl peroxides by reacting olefins with the general formula II with hydroperoxides under acid catalysis. It is essential for this process to use a medium which is completely free from water. Consequently, an anhydrous hydroperoxide must be used and the acid must be in the water-free state. When hydrochloric acid is used, this means that gaseous hydrogen chloride must be employed. Practically anhydrous hydroperoxide is complicated and dangerous to prepare. In addition, this known process required long reaction times and yet results in low yields with a low purity product.

It was, therefore, an object of the present invention to develop a process for the preparation of tert. alkyl-tert. aralkyl peroxides in the case of which the use of gaseous hydrogen chloride and anhydrous hydroperoxide is not necessary and which can be carried out within a short reaction time with high yields.

THE INVENTION

This object and other are achieved by means of a process for the preparation of tert. alkyl-tert. aralkyl peroxides with the general formula I

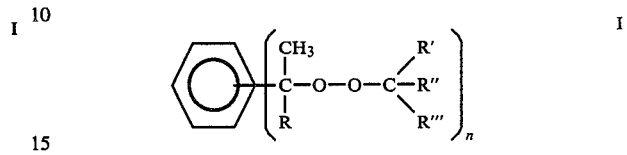

where R represents an alkyl radical with 1 to 4 C-atoms, R', R" and R"' represent the same or different alkyl radicals with 1 to 5 C-atoms and n is a number between 1 and 3, by reacting an olefin with the general formula II

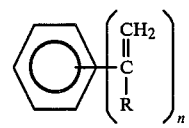

to with a tert. alkyl hydroperoxide with the general formula III

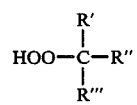

where R, R', R" and R"' and n have the meaning indicated above, in the presence of aqueous hydrochloric acid.

Surprisingly, it is possible according to the invention to prepare tert.alkyl-tert. aralkyl peroxides within a short period in high yields and with a high level of purity. Dilute hydrochloric acid and aqueous hydroperoxide can be used for the process according to the invention.

Preferably, a compound with the general formula II in which n equals 1 and R represents methyl i.e. alpha-methyl styrene is used as the olefin.

The radicals, R, R', R" and R"' are preferably alkyl radicals with 1 or 2 C-atoms.

During the execution of the process according to the invention, the tert. alkyl hydroperoxide should be present in excess compared with the olefin. Preferably, 1.5 to 2 mole tert.alkyl hydroperoxide per mole olefinic double bond are used.

The addition reaction is carried out in the presence of aqueous hydrochloric acid. The concentration of the aqueous hydrochloric acid is not critical. Any commercial-grade, dilute hydrochloric acid can be used. Preferably, the hydrochloric acid concentration is within a range of 20 to 40%, a concentration of 25 to 30% is particularly preferred.

The hydrochloric acid is used in an amount of 0.5 to 2 mole based on the olefin groups used.

The reaction can be carried out at ambient temperature. Preferably, the addition of the hydrochloric acid is effected at a temperature between 15° and 35° C. During the reaction, the temperature increases since the reaction is exothermic. The reaction takes place at normal pressure.

The separation of the reaction product takes place in the known way. If the peroxide is obtained in the crystalline form, it can be separated from the aqueous phase by filtering or centrifuging. If it is obtained in the liquid form, the organic phase can be separated from the aqueous phase by decanting. After separation, it is appropriate to subject the product obtained to an alkaline wash.

The process according to the invention supplies the desired tert.alkyl-tert.aralkyl peroxide in a purity of more than 95%. The yields are above 90%. The use of commercial quality dilute hydrochloric acid and of commercial-quality, aqueous butyl hydroperoxide are further advantages of the process according to the invention. Consequently, a process is made available which gives the desired product in a high yield and in a high purity within a short period and in a simple manner.

The process is illustrated by examples.

EXAMPLE 1

235 g of 31% hydrochloric acid (2 moles) are metered into a mixture of 238 g of alpha-methyl styrene (2 moles) and 394 g of 80% tert.butyl hydroperoxide (3.5 moles) with stirring within 15 minutes, while the temperature of the mixture is allowed to rise from 20° C. to 35° C. Subsequently, stirring is continued for a further 2 hours at 40° C. then 250 ml water are added, the mixture is allowed to stand for 15 minutes and the aqueous phase is separated off. The organic phase is washed with 250 ml of 15% sodium hydroxide solution and twice with 500 ml of water in each case. After adding 20 g of water, the product is blown out with air at 50° C. (30 minutes). 395 g of a slightly yellowish liquid with a content of 96% tert.butyl cumyl peroxide and less than 0.4% alpha-methyl styrene are obtained. This corresponds to a yield of 91% based on the alpha-methyl styrene used.

EXAMPLE 2

317 g of 1,4-diisopropenyl benzene (2 moles) are dissolved in 900 g of 80% tert.butyl hydroperoxide (8 moles). 1 ml of a wetting agent (dodecyl benzene sulphonic acid) is added and 470 g of 31% hydrochloric acid (4 moles) are then added with stirring at 35° C. while the temperature of the mixture rises to as much as 45° C. After approximately 10 minutes, the peroxide begins to crystallize out. Stirring is continued for 20 minutes at 40° C. and the mother liquor is then largely separated off from the supernatant peroxide. 1 liter of 12% sodium hydroxide solution is added, to the remaining portion and stirred for 10 minutes at 30° to 40° C., cooled to 20° C. and filtered. The solid is washed with water to neutrality on the suction filter and dried at room temperature. 590 g of an almost white powder with a content of 96% of 1,4 bis-(tert.butyl peroxy isopropyl) benzene (84% of the theoretical yield) are obtained.

REFERENCE EXAMPLE 3

According to example 3 of GB-PS No. 954 361, 0.1 mole of dry hydrogen chloride gas in 1.15 mole alpha-methyl styrene were reacted with 1 mole of 98% tert.-butyl hydroperoxide. The reaction took 5 hours and was carried out at 50° C. After washing and drying, 177.3 g of crude product were obtained which, according to GC analysis, had a content of 70.7% tert.butyl cumyl peroxide and 25.8 unreacted alpha-methyl styrene apart from a small proportion of other impurities. By blowing out with air at 50° C. after adding 5% by wt. water, 145 g of a liquid with a content of 83.9% tert.butyl cumyl peroxide and 13% alpha-methyl styrene were obtained. This corresponds to a tert.butyl cumyl peroxide yield of 58% based on the tert.butyl hydroperoxide used and of 50% based on the alpha-methyl styrene used.

Consequently, a poor yield and a lower level of purity of the product is obtained in the case of the known processes in spite of the use of 98% tert.butyl hydroperoxide with a long reaction period.

It will be understood that the specification and examples are illustrative but not limitative of the present invention and that other embodiments within the spirit and scope of the invention will suggest themselves to those skilled in the art.

I claim:

1. A process for the preparation of tert.alkyl-tert.aralkyl peroxides of the general formula

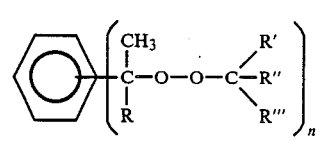

where R represents an alkyl radical with 1 to 4 C-atoms, R', R" and R'" represent the same or different alkyl radicals with 1 to 5 C-atoms and n is a number between 1 and 3, comprising: reacting an olefin of the general formula

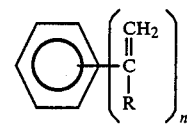

with a tert.alkyl hydroperoxide of the general formula

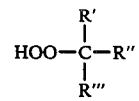

where R, R', R" and R'" and n have the meaning indicated above, in the presence of aqueous hydrochloric acid in an amount of 0.5 to 2 mole of the hydrochloric acid per mole of olefinic double bond.

2. The process of claim 1 wherein the hydrochloric acid is used in a concentration of 20 to 40 wt.-%.

3. The process of claim 1 wherein the hydrochloric acid is used in a concentration of 25 to 37 wt.-%.

4. The process of claim 2 wherein the hydrochloric acid is used in a concentration of 25 to 37 wt.-%.

5. The process of claim 1 wherein the olefin of general formula II is an alpha-methyl styrene.

6. The process of claim 1 wherein the tert.alkyl hydroperoxide is tert.butyl hydroperoxide.

7. The process of claim 1 wherein the reaction is carried out at ambient temperatures.

8. The process of claim 1 wherein the reaction is carried out at a temperature in the range of from 15° C. to 35° C.

9. The process of claim 1 wherein the reaction is carried out at a temperature in the range of from 15° C. to 45° C.

10. The process of claim 1 wherein R, R', R" and R'" are independently alkyls of 1 or 2 carbon atoms.

11. The process of claim 1 wherein the reaction is carried out with 1.5 to 2 moles of the tert.alkyl hydroperoxide per mole of olefinic double bond.

* * * * *